United States Patent [19]

Hayes

[11] 3,936,369

[45] Feb. 3, 1976

[54] HYDROCARBON CONVERSION WITH A SULFIDED CATALYTIC COMPOSITE

[75] Inventor: John C. Hayes, Palatine, Ill.

[73] Assignee: Universal Oil Products Company, Des Plaines, Ill.

[22] Filed: Sept. 30, 1974

[21] Appl. No.: 510,255

Related U.S. Application Data

[63] Continuation-in-part of Ser. No. 365,782, May 31, 1973, Pat. No. 3,839,193, which is a continuation-in-part of Ser. No. 27,457, April 10, 1970, abandoned.

[52] U.S. Cl............. 208/139; 252/439; 252/466 PT
[51] Int. Cl.².................. C10G 35/08; B01J 11/12
[58] Field of Search ............ 208/138, 139; 252/439, 252/466 PT

[56] References Cited
UNITED STATES PATENTS

| | | | |
|---|---|---|---|
| 2,848,377 | 8/1958 | Webb................................ | 208/138 |
| 2,906,700 | 9/1969 | Stine et al.......................... | 208/138 |
| 3,642,660 | 2/1972 | Mitsche ............................. | 208/138 |
| 3,670,040 | 6/1972 | Drehman et al.................... | 208/138 |

*Primary Examiner*—Herbert Levine
*Attorney, Agent, or Firm*—James R. Hoatson, Jr.; Thomas K. McBride; William H. Page, II

[57] ABSTRACT

The performance of a hydrocarbon conversion process using a trimetallic acidic catalytic composite, comprising a combination of catalytically effective amounts of a platinum or palladium component, an iridium component, a germanium component, and a halogen component with a porous carrier material, is improved by sulfiding the catalytic component, prior to any contact with hydrocarbon, so that about 0.05 to 0.5 wt. % of sulfur is incorporated therein, thereby diminishing undesired exothermic hydrocracking and demethylation during initial operation of the process.

8 Claims, No Drawings

HYDROCARBON CONVERSION WITH A SULFIDED CATALYTIC COMPOSITE

CROSS-REFERENCES TO RELATED APPLICATIONS

This application is a continuation-in-part of my prior, copending application Ser. No. 365,782 filed May 31, 1973, now patent no. 3,839,193, which in turn in a continuation-in-part of my prior, now abandoned, application Ser. No. 27,457 filed April 10, 1970. All of the teachings of these prior applications are incorporated herein by reference.

The subject of the present invention is a novel acidic sulfided trimetallic catalytic composite which has exceptional activity and resistance to deactivation when employed in a hydrocarbon conversion process that requires a catalyst having both a hydrogenation-dehydrogenation function and a cracking function. More precisely, the present invention involves a novel dual-function, acidic, trimetallic, and sulfided catalytic composite which, quite surprisingly, enables substantial improvements in hydrocarbon conversion processes that have traditionally used a dual-function catalyst. In another aspect, the present invention comprehends the improved processes that are produced by the use of a sulfided catalytic composite comprising a combination of catalytically effective amounts of a platinum or palladium component, an iridium component, a germanium component, and a halogen component with a porous carrier material; specifically, an improved reforming process which utilizes the subject catalyst to improvde activity, selectivity, and stability characteristics.

Composites having a hydrogenation-dehydrogenation function and a cracking function are widely used today as catalysts in many industries, such as the petroleum and petrochemical industry, to accelerate a wide spectrum of hydrocarbon conversion reactions. Generally, the cracking function is thought to be associated with an acid-acting material of the porous, adsorptive, refractory oxide type which is typically utilized as the support or carrier for a heavy metal component such as the metals or compounds of metals of Groups V through VIII of the Periodic Table to which are generally attributed the hydrogenation-dehydrogenation function.

These catalytic composites are used to accelerate a wide variety of hydrocarbon conversion reactions such as hydrocracking, isomerization, dehydrogenation, hydrogenation, desulfurization, cyclization, alkylation, polymerization, cracking, hydroisomerization, etc. In many cases, the commercial applications of these catalysts are in processes where more than one of these reactions are proceeding simultaneously. An example of this type of process is reforming wherein a hydrocarbon feed stream containing paraffins and naphthenes is subjected to conditions which promote dehydrogenation of naphthenes to aromatics, dehydrocyclization of paraffins to aromatics, isomerization of paraffins and naphthenes, hydrocracking of naphthenes and paraffins and the like reactions to produce an octane-rich or aromatic-rich product stream. Another example is a hydrocracking process wherein catalysts of this type are utilized to effect selective hydrogenation and cracking of high molecular weight unsaturated materials, selective hydrocracking of high molecular weight materials, and other like reactions, to produce a generally lower boiling, more valuable output stream. Yet another example is an isomerization process wherein a hydrocarbon fraction which is relatively rich in straight-chain paraffin components is contacted with a dual-function catalyst to produce an output stream rich in isoparafin compounds.

Regardless of the reaction involved or the particular process involved, it is of critical importance that the dual-function catalyst exhibit not only the capability to initially perform its specified functions, but also that it has the capability to perform them satisfactorily for prolonged periods of time. The analytical terms used in the art to measure how well a particular catalyst performs its intended functions in a particular hydrocarbon reaction environment are activity, selectivity, and stability. And for purposes of discussion here, these terms are conveniently defined for a given charge stock as follows: (1) activity is a measure of the catalyst's ability to convert hydrocarbon reactants into products at a specified severity level where severity level means the conditions used--that is, the temperature, pressure, contact time, and presence of diluents such as $H_2$; (2) selectivity refers to the amount of desired product or products obtained relative to the amount of reactants charged or converted; (3) stability refers to the rate of change with time of the activity and selectivity parameters--obviously, the smaller rate implying the more stable catalyst. In a reforming process, for example, activity commonly refers to the amount of conversion that takes place for a given charge stock at a specified severity level and is typically measured by octane number of the $C_5+$ product stream; selectivity refers to the amount of $C_5+$ yield relative to the amount of the charge that is obtained at the particular activity or severity level; and stability is typically equated to the rate of change with time of activity, as measured by octane number of $C_5+$ product, and of selectivity, as measured by $C_5+$ yield. Actually, the last statement is not strictly correct because generally a continuous reforming process is run to produce a constant octane $C_5+$ product with severity level being continuously adjusted to attain this result; and, furthermore, the severity level is for this process usually varied by adjusting the conversion temperature in the reaction zone so that, in point of fact, the rate of change of activity finds response in the rate of change of conversion temperatures and changes in this last parameter are customarily taken as indicative of activity stability.

As is well known to those skilled in the art, the principal cause of observed deactivation or instability of a dual-function catalyst when it is used in a hydrocarbon conversion reaction is associated with the fact that coke forms on the surface of the catalyst during the course of the reaction. More specifically, in thse hydrocarbon conversion processes, the conditions utilized typically result in the formation of heavy, high molecular weight, black, solid or semi-solid, carbonaceous material which coats the surface of the catalyst and reduces its activity by shielding its active sites from the reactants. In order words the performance of this dual-function catalyst is sensitive to the presence of carbonaceous deposites on the surface of the catalyst. Accordingly, the major problem facing workers in this area of the art is the development of more active and selective catalytic composites that are not sensitive to the presence of these carbonaceous materials and/or have the capability to suppress the rate of the formation of these carbonaceous materials on the catalyst.

Viewed in terms of performance parameters, the problem is to develop a dual-function catalyst having superior activity, selectivity, and stability. In particular, for a reforming process the problem is typically expressed in terns of shifting and stabilizing the $C_5+$ yield octane relationship—$C_5+$ yield being representative of selectivity and octane being proportional to activity.

I have now found an improvement in a dual-function trimetallic acidic catalytic composite which possesses improved activity, selectivity, and stability characteristics when it is employed in a process for the conversion of hydrocarbons of the type which have heretofore utilized dual-function acidic catlytic composites such as processes for isomerization, hydroisomerization, dehydrogenation, desulfurization, denitrogenization, hydrogenation, alkylation, dealkylation, hydrodealkylation, transalkylation, cyclization, dehydrocyclization, cracking, hydrocracking, reforming, and the like processes. In particular, I have ascertained that a catalyst, comprising a sulfided combination of catalytically effective amounts of a platinum or palladium component, an iridium component, a germanium componet, and a halogen component with a porous refractory carrier material, can enable the performance of hydrocarbon conversion processes utilizing dual-function catalysts to be substantially improved if the metallic components are uniformly dispersed throughout the carrier material, if their oxidation states are controlled to be in the states hereinafter specified, and if the catalyst is sulfided in the manner indicated herein before use in the conversion of hydrocarbons. Moreover, I have determined, as will be hereinafter demonstrated, that an acidic sulfided catalytic composite, comprising a combination of catalytically effective amounts of a platinum or palladium component, a germanium component, an iridium component, and a chloride component with an alumina carrier material, can be utilized to substantially improve the performance of a reforming process which operates on a low-octane gasoline fraction to produce a high-octane reformate if the metallic components are uniformly distributed throughout the alumina carrier material, if their oxidation states are fixed in the states hereinafter specified, and if the catalyst is properly sulfided before use in the conversion of hydrocarbons. In the case of a reforming process, the principal advantage associated with the use of the sulfided catalyst of the present invention involves the acquisition of the capability to operate in a stable manner in a high severity operation; for example, an intermediate pressure reforming process designed to produce a $C_5+$ reformate having an octane of about 100 F-1 clear. As indicated, the present invention essentially involves the finding that the addition of a germanium component and an iridium component to a dual-function acid hydrocarbon conversion catalyst containing a platinum or palladium component can enable the performance characteristics of the catalyst to be sharply and materially improved, if the hereinafter specified limitations on amounts of ingredients, oxidation states of metals, distribution of metallic components in the support and sulfiding are met.

It is accordingly, one subject of the present invention to provide an improvement in a trimetallic hydrocarbon conversion catalyst having superior performance characteristics when utilized in a hydrocarbon conversion process. A second object is to provide a sulfided catalyst having dual-function hydrocarbon conversion performance characteristics that are relatively insensitive to the deposition of hydrocarbonaceous material thereon. A third object is to provide preferred methods of preparation of this sulfided catalytic composite which insures the achievement and maintenance of its properties. Another object is to provide an improved reforming catalyst having superior activity, selectivity, and stability. Yet another object is to provide a dual-function sulfided hydrocarbon conversion catalyst which utilizes a combination of a germanium component and an iridium component to promote an acidic catalyst containing a platinum or palladium metal component.

In brief summary, the present invention is, in one embodiment, an improvement in a process for converting a hydrocarbon which comprises contacting the hydrocarbon, at hydrocarbon conversion conditions with a catalytic composite comprising a porous carrier material containing, on an elemental basis, about 0.01 to about 2 wt. % platinum or palladium metal, about 0.01 to 2 wt. % iridium metal, about 0.01 to about 5 wt. % germanium, and about 0.1 to about 3.5 wt. % halogen, wherein the platinum or palladium, germanium, and iridium are uniformly dispersed throughout the porous carrier material, wherein substantially all of the platinum or palladium and iridium are present in the corresponding elemental metallic state and wherein substantially all of the germanium is present in an oxidation state above that of the elemental metal. The improvement in this process relates to sulfiding the catalytic composite, prior to contact with the hydrocarbon, with a sulfiding gas at sulfiding conditions selected to incorporate about 0.5 to about 0.5 wt. % sulfur.

A second embodiment relates to a sulfided catalytic composite comprising a porous carrier material containing, on an elemental basis, about 0.01 to about 2 wt. % platinum or palladium metal, about 0.01 to about 2 wt. % iridium metal, about 0.01 to about 5 wt. % germanium, about 0.1 to about 3.5 wt. % halogen, and about 0.05 to about 0.5 wt. % sulfur, wherein the platinum or palladium, germanium, and iridium are uniformly dispersed throughout the porous carrier material, wherein substantially all of the platinum or palladium and iridium are present in the corresponding elemental metallic state or in a sulfided state, wherein substantially all of the germanium is present in an oxidation state above that of the elemental metal and wherein the catalytic composite is sulfided prior to use in the conversion of hydrocarbons.

Yet another embodiment relates to a process for the conversion of a hydrocarbon comprising contacting the hydrocarbon and hydrogen with the sulfided catalytic composite described above in the second embodiment at hydrocarbon conversion conditions.

A preferred embodiment relates to a process for reforming a gasoline fraction which comprises contacting the gasoline fraction and hydrogen with the sulfided catalytic composite described above in the second embodiment at reforming conditions selected to produce a high-octane reformate.

Other objects and embodiments of the present invention relate to additional details regarding preferred catalytic ingredients, preferred amounts of ingredients, suitable methods of composite preparation, operating conditions for use in the hydrocarbon conversion processes, and the like particulars which are hereinafter given in the following detailed discussion of each of these facets of the present invention.

The sulfided trimetallic catalyst of the present invention comprises a porous carrier material or support having combined therewith catalytically effective amounts of a platinum or palladium component, an iridium component, a germanium component, and a halogen component.

Considering first the porous carrier material utilized in the present invention, it is preferred that the material be a porous, adsorptive, high-surface area support having a surface area of about 25 to about 500 m²/g. The porous carrier material should be relatively refractory to the conditions utilized in the hydrocarbon conversion process, and it is intended to include within the scope of the present invention carrier materials which have traditionally been utilized in dual-function hydrocarbon conversion catalysts such as: (1) activated carbon, coke, or charcoal; (2) silica or silica gel, silicon carbide, clays, and silicates including those synthetically-prepared and naturally-occurring, which may or may not be acid treated, for example, attapulgus clay, china clay, diatomaceous earth, fuller's earth, kaoline, kieselguhr, etc.; (3) ceramics, porcelain, crushed firebrick, bauxite; (4) refractory inorganic oxides such as alumina, titanium dioxide, zirconium dioxide, chromium oxide, zinc oxide, magnesia, thoria, boria, silica-alumina, silica-magnesia, chromia-alumina, alumina-boria, silica zirconia, etcl; (5) crystalline zeolitic aluminosilicates such as naturally-occuring or synthetically-prepared mordenite and/or faujasite, either in the hydrogen form or in a form which has been treated with multi-valent cations; ( 6) spinels such as $MgAl_2O_4$, $FeAl_2O_4$, $ZnAl_2O_4$, $MnAl_2O_4$, $CaAl_2O_4$ and other like compounds having the formula $Mo \cdot Al_2O_3$ where M is a metal having a valence of 2; and (7) combinations of elements from one or more of these groups. The preferred porous carrier materials for use in the present invention are refractory inorganic oxides, with best results obtained with an alumina carrier material. Suitable alumina materials are the crystalline alumina known as the gamma-, eta-, and theta-alumina, with gamma- or eta-alumina giving the best results. In addition, in some embodiments the alumina carrier material may contain minor proportions of other well known refractory inorganic oxides such as silica, zirconia, magnesia, etc.; however, the preferred support is substantially pure gamma-, or eta-alumina. Preferred carrier materials have an apparent bulk density of about 0.3 to about 0.7 g/cc and surface area characteristics such that the average pore diameter is about 20 to 300 Angstroms, the pore volume is about 0.1 to about 1 cc/g, and the surface area is about 100 to about 500 m²/g. In general, best results are typically obtained with a gamma-alumina carrier material which is used in the form of spherical particles having: a relatively small diameter (i.e. typically about one-sixteenth inch), an apparent bulk density of about 0.5 to about 0.6 g/cc, a pore volume of about 0.4 ml/g, and a surface area of about 175 m²/g.

The preferred alumina carrier material may be prepared in any suitable manner and may be synthetically prepared or natural occurring Whatever type of alumina is employed it may be activated prior to use by one or more treatments including drying, calcination, steaming, etc., and it may be in a form known as activated alumina, activated alumina of commerce, porous alumina, alumina gel, etc. For example, the alumina carrier may be prepared by adding a suitable alkaline reagent such as ammonium hydroxide to a salt of aluminum such as aluminum chloride, alumina nitrate, etc., in an amount to form an aluminum hydroxide gel which upon drying and calcining is converted to alumina. The alumina carrier may be formed in any desired shape such as spheres, pills, cakes, extrudates, powders, granules, tablets, etc., and utilized in any desired size. For the purpose of the present invention, a particularly preferred form of alumina is the sphere; and alumina spheres may be continuously manufactured by the well known oil drop method which comprises: forming an alumina hydrosol by any of the techniques taught in the art and preferably by reacting aluminum metal with hydrochloric acid, combining the resulting hydrosol with a suitable gelling agent and dropping the resultant mixture into an oil bath maintained at elevated temperatures. The droplets of the mixture remain in the oil bath until they set and form hydrogel spheres. The spheres are then continuously withdrawn from the oil bath and typically subjected to specific aging treatments in oil and an ammoniacal solution to further improve their physical characteristics. The resulting aged and gelled particles are then washed and dried at a relatively low temperature of about 300° to about 400° F. and subjected to a calcination procedure at a temperature of about 850° F. to about 1,300° F. for a period of about 1 to about 20 hours. This treatment effects conversion of the alumina hydrogel to the corresponding crystalline gamma-alumina. See the teachings of U.S. Pat. No. 2,620,314 for additional details.

One essential constituent of the trimetallic catalyst of the present invention is a germanium component. It is an essential feature of the present invention that substantially all of the germanium component is present in the catalyst in an oxidation state above that of the elemental metal. This component may exist within the composite as a compound such as the oxide, sulfide, halide, oxychloride, aluminate, etc., or in combination with the carrier material or other ingredients of the composite. Although it is not intended to restrict the present invention by this explanation, it is believed that best results are obtained when the germanium component is present in the composite in the +2 or +4 oxidation state, with the +4 oxidation state being preferred. Preferably, the germanium component is used in an amount sufficient to result in the final catalytic composite containing, on an elemental basis, about 0.01 to about 5 wt. % germanium, with best results typically obtained with about 0.05 to about 2 wt. % germanium.

This germanium component may be incorporated in the catalytic composite in any suitable manner known to the art to result in a uniform dispersion of the metal moiety throughout the carrier material such as by coprecipitation or cogellation with the porous carrier material, ion-exchange with the gelled carrier material, or impregnation of the carrier material either after or before it is dried and calcined. It is to be noted that it is intended to include within the scope of the present invention all conventional methods for uniformly distributing a metallic component in a catalytic composite and the particular method of incorporation used is not deemed to be an essential feature of the present invention. One method of incorporating the germanium component into the catalytic composite involves coprecipitating the germanium component during the preparation of the preferred carrier material, alumina. This method typically involves the addition of a suitable germanium compound such as germanium tetrachloride or finely divided germanium oxide to the alumina hydrosol and then combining the hydrosol with a suitable gelling agent and dropping the resulting mixture into an oil bath, etc., as explained in detail hereinbefore. After drying and calcining the resulting gelled carrier material there is obtained an intimate combination of alumina and germanium oxide. A preferred method of incorporating the germanium component into the catalytic composite involves utilization of a soluble, decomposable compound of germanium to impregnate the porous carrier material. In general, the solvent used in this impregnation step is selected on the basis of the capability to dissolve the desired germanium compound and is preferably an aqueous, acidic solution. Thus, the germanium component may be added to the carrier material by commingling the latter with an aqueous, acidic solution of suitable germanium salt or suitable compound of germanium such as germanium oxide, germanium tetraethoxide, germanium tetrapropoxide, germanium tetrachloride, germanium difluoride, germanium tetrafluoride, germanium diiodide, germanium monosulfide, and the like compounds. One particularly preferred impregnation solution comprises nascent germanium metal dissolved in chlorine water to yield a germanium oxychloride. A second preferred impregnation solution comprises germanium tetrachloride dissolved in an anhydrous alcohol such as ethanol or propanol. In general, the germanium component can be impregnated either prior to, simultaneously with, or after the other metallic components are added to the carrier material. However, I have found excellent results when the germanium component is impregnated simultaneously with the other metallic components. In fact, I have determined that a preferred impregnation solution comprises chloroplatinic acid, hydrogen chloride, chloroiridic acid, and germanium tetrachloride dissolved in ethanaol. Best results are believed to be obtained when this component exists in the composite as germanium oxide.

Regardless of which germanium compound is used in the preferred impregnation step, it is important that the germanium component be uniformly distributed throughout the carrier material. In order to achieve this objective, it is necessary to maintain the pH of the impregnation solution in a range of about 1 to about 7 and to dilute the impregnation solution to a volume which approximates the volume of the carrier material which is impregnated. It is preferred to use a volume ratio of impregnation solution to carrier material of at least 0.5:1 and preferably about 1:1 to about 10:1 or more. Similarly, it is preferred to use a relatively long contact time during the impregnation step ranging from about ¼ hour up to about ½ hour or more before drying to remove excess solvent in order to insure a high dispersion of the germanium component through the carrier material. The mixture of impregnation solution and carrier material is, likewise, preferably constantly agitated during this preferred impregnation step.

A second essential ingredient of the subject catalyst is the platinum or palladium component. That is, it is intended to cover the use of platinum or palladium or mixtures thereof as a second component of the present composite. It is an essential feature of the present invention that substantially all of this platinum or palladium component exists within the final catalytic composite in the elemental metallic state or in a sulfided state. Generally, the amount of this component present in the final catalyst composite is small compared to the quantities of the other components combined therewith. In fact, the platinum or palladium component generally will comprise about 0.01 to about 2 wt. % of the final catalytic composite, calculated on an elemental basis. Excellent results are obtained when the catalyst contains about 0.05 to about 1 wt. % of the platinum or palladium metal.

This platinum or palladium component may be incorporated in the catalytic composite in any suitable manner known to result in a relatively uniform distribution of this component in the carrier material such as coprecipitation or cogellation, ion-exhange, or impregnation. The preferred method of preparing the catalyst involves the utilization of a soluble, decomposable compound of platinum or palladium to impregnate the carrier material in a relatively uniform manner. For example, this component may be added to the support by commingling the latter with an aqueous solution of chloroplatinic or chloropalladic acid. Other water-soluble compounds of platinum or palladium may be employed in impregnation solutions and include ammonium chloroplatinate, bromoplatinic acid, platinum dichloride, platinum tetrachloride hydrate, platinum dichlorocarbonyl dichloride, dinitrodiaminoplatinum, palladium chloride, palladium nitrate, palladium sulfate, etc. The utilization of a platinum or palladium chloride compound, such as chloroplatinic or chloropalladic acid, is preferred since it facilitates the incorporation of both the platinum or palladium component and at least a minor quantity of the preferred halogen component in a single step. Hydrogen chloride or the like acid is also generally added to the impregnation solution in order to further facilitate the incorporation of the halogen component and the uniform distribution of the metallic component throughout the carrier material. In addition, it is generally preferred to impregnate the carrier material after it has been calcined in order to minimize the risk of washing away the valuable platinum or palladium compounds; however, in some cases it may be advantageous to impregnate the carrier material when it is in a gelled state.

Yet another essential ingredient of the present catalytic composite is an iridium component. It is of fundamental importance that substantially all of the iridium component exists within the catalytic composite of the present invention in the elemental state or in a sulfided state and the subsequently described reduction and sulfiding procedure is designed to accomplish this objective. The iridium component may be utilized in the composite in any amount which is catalytically effective, with the preferred amount being about 0.01 to about 2 wt. % thereof, calculated on an elemental iridium basis. Typically, best results are obtained with about 0.05 to about 1 wt. % iridium. It is, additionally, preferred to select the specific amount of iridium from within this broad weight range as a function of the amount of the platinum or palladium component, on an atomic basis, as is explained hereinafter.

This iridium component may be incorporated into the catalytic composite in any suitable manner known to those skilled in the catalyst formulation art which results in a relatively uniform dispersion of iridium in the carrier material. In addition, it may be added at any stage of the preparation of the composite—either during preparation of the carrier material or thereafter—and the precise method of incorporation used is not deemed to be critical. However, best results are thought to be obtained when the iridium component is relatively uniformly distributed throughout the carrier material, and the preferred procedures are the ones known to result in a composite having this relatively uniform distribution. One acceptable procedure for incorporating this component into the composite involves cogelling or coprecipitating the iridium component during the preparation of the preferred carrier material, alumina. This procedure usually comprehends the addition of a soluble, decomposable compound of iridium such as iridium tetrachloride to the alumina hydrosol before it is gelled. The resulting mixture is then finished by conventional gelling, aging, drying, and calcination steps as explained hereinbefore. A preferred way of incorporating this component is an impregnation step wherein the porous carrier material is impregnated with a suitable iridium-containing solution either before, during, or after the carrier material is calcined. Preferred impregnation solutions are aqueous solutions of water soluble, decomposable iridium compounds, such as iridium tribromide, iridium dichloride, iridium tetrachloride, iridium oxalic acid, iridium sulfate, potassium iridochloride, chloroiridic acid, and the like compounds. Best results are ordinarily obtained when the impregnation solution is an aqueous solution of chloroiridic acid or sodium chloroiridate. This component can be added to the carrier material, either prior to, simultaneously with, or after the other metallic components are combined therewith. Best results are usually achieved when this component is added simultaneously with the other metallic components. In fact, excellent results are obtained, as reported in the examples, with a one step impregnation procedure using an aqueous solution comprising chloroplatinic or chloropalladic acid, chloroiridic acid, hydrochloric acid, and germanium tetrachloride dissolved in anhydrous alcohol.

It is essential to incorporate a halogen component into the trimetallic catalytic composite of the present invention. Although the precise form of the chemistry of the association of the halogen component with the carrier material is not entirely known, it is customary in the art to refer to the halogen component as being combined with the carrier material, or with the other ingredients of the catalyst in the form of the halide (e.g. as the chloride). This combined halogen may be either fluorine, chlorine, iodine, bromine, or mixtures thereof. Of these, fluorine and, particularly, chlorine are preferred for the purposes of the present invention. The halogen may be added to the carrier material in any suitable manner, either during preparation of the support or before or after the addition of the other components. For example, the halogen may be added, at any stage of the preparation of the carrier material or to the calcined carrier material, as an aqueous solution of a suitable, decomposable halogen-containing compound such as hydrogen, fluoride, hydrogen chloride, hydrogen bromide, ammonium chloride, etc. The halogen component or a portion thereof, may be combined with the carrier material during the impregnation of the latter with the platinum or palladium or iridium components; for example, through the utilization of a mixture of chloroplatinic acid and hydrogen chloride. In another situation, the alumina hydrosol which is typically utilized to form the preferred alumina carrier material may contain halogen and thus contribute at least a portion of the halogen component to the final composite. For reforming, the halogen will be typically combined with the carrier material in an amount sufficient to result in a final composite that contains about 0.1 to about 3.5%, and preferably about 0.5 to about 1.5% by weight of halogen calculated on an elemental basis. In isomerization or hydrocracking embodiments, it is generalaly preferred to utilize relatively larger amounts of halogen in the catalyst—typically, ranging up to about 10 wt. % halogen calculated on an elemental basis, and more preferably about 1 to about 5 wt. %.

Regarding the preferred amounts of the various metallic components of the subject catalyst, I have found it to be a good practice to specify the amounts of the iridium component and the germanium component as a function of the amount of the platinum or palladium component. On this basis, the amount of the iridium component is ordinarily selected so that the atomic ratio of iridium to platinum or palladium metal contained in the composite is about 0.1:1 to about 2:1, with the preferred range being about 0.25:1 to about 1.5:1. Similarly, the amount of the germanium component is ordinarily selected to produce a composite containing an atomic ratio of germanium to platinum or palladium metal of about 0.3:1 to about 10:1, with the preferred range being about 0.6:1 to about 6:1.

Another significant parameter for the instant catalyst is the "total metals content" which is defined to be the sum of the platinum or palladium component, the iridium component, and the germanium component, calculated on an elemental metal basis. Good results are ordinarily obtained with the subject catalyst when this parameter is fixed at a value of about 0.15 to about 3 wt. %, with best results ordinarily achieved at a metals loading of about 0.3 to about 2 wt. %.

In embodiments of the present invention wherein the instant trimetallic catalytic composite is used for dehydrogenation of dehydrogenatable hydrocarbons or for the hydrogenation of hydrogenatable hydrocarbons, it is ordinarily a preferred practice to include an alkali or alkaline earth metal component in the composite. More precisely, this optional component is selected from the group consisting of the compounds of the alkali metal—cesium, rubidium, potassium, sodium, and lithium— and the compounds of the alkaline earth metals—calcium, strontium, barium, and magnesium. Generally, good results are obtained in these embodiments when this component constitutes about 1 to about 5 wt. % of the composite, calculated on an elemental basis. This optional alkali or alkaline earth metal component can be incorporated in the composite in any of the known ways, with impregnation with an aqueous solution of a suitable water-soluble, decomposable compound being preferred.

An optional ingredient for the trimetallic catalyst of the present invention is a Friedel-Crafts metal halide component. This ingredient is particularly useful in hydrocarbon conversion embodiments of the present invention wherein it is preferred that the catalyst utilized has a strong acid or cracking function associated therewith—for example, an embodiment wherein hydrocarbons are to be hydrocracked or isomerized with the catalyst of the present invention. Suitable metal halides of the Friedel-Crafts type include aluminum chloride, aluminum bromide, ferric chloride, ferric bromide, zinc chloride, and the like compounds, with the aluminum halides and particularly aluminum chloride ordinarily yielding best results. Generally, this optional ingredient can be incorporated into the composite of the present invention by any of the conventional methods for adding metallic halides of this type;

however, best results are ordinarily obtained when the metallic halide is sublimed onto the surface of the carrier material according to the preferred method disclosed in U.S. Pat. No. 2,999,074. The component can generally be utilized in any amount which is catalytically effective with a value selected from the range of about 1 to about 100 wt. % of the carrier material generally being preferred.

Regardless of the details of how the components of the catalyst are combined with the porous carrier material, the final catalyst generally will be dried at a temperature of about 200° to about 600° F. for a period of at least about 2 to about 24 hours or more, and finally calcined or oxidized at a temperature of about 700° F. to about 1100° F. in an air atmosphere for a period of about 0.5 to about 10 hours in order to convert substantially all of the metallic components substantially to the oxide form. Because a halogen component is utilized in the catalyst, best results are generally obtained when the halogen contact of the catalyst is adjusted during the calcination step by including a halogen or a halogen-containing compound in the air atmosphere utilized. In particular, when the halogen component of the catalyst is chlorine, it is preferred to use a mole ratio of $H_2O$ to HCl of about 5:1 to about 100:1 during at least a portion of the calcination step in order to adjust the final chlorine content of the catalyst to a range of about 0.1 to about 3.5 wt. %.

It is an essential feature of the present invention that the resultant oxidized catalytic composite is subjected to a substantially water-free reduction step prior to its use in the conversion of hydrocarbons. This step is designed to selectively reduce the platinum or palladium and iridium components to the corresponding metals and to insure a uniform and finely divided dispersion of these metallic components throughout the carrier material, while maintaining the germanium component in a positive oxidation state. Preferably, substantially pure and dry hydrogen (i.e. less than 20 vol. ppm. $H_2O$) is used as the reducing agent in this step. The reducing agent is contacted with the oxidized catalyst at conditions including a temperature of about 800° to about 1,200° F. and a period of time of about 0.5 to 2 hours effective to reduce substantially all of the platinum or palladium and iridium components to their elemental metallic state while maintaining the germanium component in an oxidation state above that of the elemental metal. This reduction treatment may be performed in situ as part of a start-up sequence if precautions are takenn to predry the plant to a substantially water-free state and if substantially water-free hydrogen is used.

Another feature of the instant invention involves recognition that the resulting reduced catalytic composite can be beneficially subjected to a presulfiding operation designed to incorporate in the catalytic composite from about 0.05 to about 0.5 wt. % sulfur calculated on an elemental basis. This presulfiding procedure is performed prior to use of the catalytic composite in the conversion of hydrocarbons. Preferably, this presulfiding treatment takes place in the presence of hydrogen and a suitable sulfur-containing compound such as hydrogen sulfide, lower molecular weight mercaptans, organic sulfides, etc. Typically, this procedure comprises treating the selectively reduced catalyst with a sulfiding gas such as a mixture of hydrogen and hydrogen sulfide having about 10 moles of hydrogen per mole of hydrogen sulfide at conditions sufficient to effect the desired incorporation of sulfur, generally including a temperature ranging from about 50° up to about 1100° F. or more. It is generally a good practice to perform this presulfiding step under substantially water-free conditions.

According to the present invention, a hydrocarbon charge stock and hydrogen are contacted with a trimetallic catalyst of the type described above in a hydrocarbon conversion zone. This contacting may be accomplished by using the catalyst in a fixed bed system, a moving bed system, a fluidized bed system, or in a batch type operation; however, in view of the danger of attrition losses of the valuable catalyst and of well known operational advantages, it is preferred to use a fixed bed system. In this system, a hydrogen-rich gas and the charge stock are preheated by any suitable heating means to the desired reaction temperature and then are passed, into a conversion zone containing a fixed bed of the catalyst type previously characterized. It is, of course, understood that the conversion zone may be one or more separate reactors with suitable means therebetween to insure that the desired conversion temperature is maintained at the entrance to each reactor. It is also important to note that the reactants may be contacted with the catalyst bed in either upward, downward, or radial flow fashion with the latter being preferred. In addition, the reactants may be in the liquid phase, a mixed liquid-vapor phase, or a vapor phase when they contact the catalyst, with best results obtained in the vapor phase.

In the case where the trimetallic catalyst of the present invention is used in a reforming operation, the reforming system will comprise a reforming zone containing a fixed bed of the catalyst type previously characterized. This reforming zone may be one or more separate reactors with suitable heating means therebetween to compensate for the endothermic nature of the reactions that take place in each catalyst bed. The hydrocarbon feed stream that is charged to this reforming system will comprise hydrocarbon fractions containing naphthenes and paraffins that boil within the gasoline range. The preferred charge stocks are those consisting essentially of naphthenes and paraffins, although in some cases aromatics and/or olefins may also be present. This preferred class includes straight run gasolines, natural gasolines, synthetic gasolines, and the like. On the other hand, it is frequently advantageous to charge thermally or catalytically cracked gasolines or higher boiling fractions thereof. Mixtures of straight run and cracked gasolines can also be used to advantage. The gasoline charge stock may be a full boiling gasoline having an initial boiling point of from about 50° to about 150° F. and an end boiling point within the range of from about 325° to about 425° F., or may be a selected fraction thereof which generally will be a higher boiling fraction commonly referred to as a heavy naphtha—for example, a naphtha boiling in the range of $C_7$ to 400° F. In some cases, it is also advantageous to charge pure hydrocarbons or mixtures of hydrocarbons that have been extracted from hydrocarbon distillates—for example, straight-chain paraffins—which are to be converted to aromatics. It is preferred that these charge stocks be treated by conventional catalytic pretreatment methods such as hydrorefining, hydrotreating, hydrodesulfurization, etc., to remove substantially all sulfurous, nitrogenous and water-yielding contaminants therefrom and to saturate any olefins that may be contained therein.

In other hydrocarbon conversion embodiments, the charge stock will be of the conventional type customarily used for the particular kind of hydrocarbon conversion being effected. For example, in a typical isomerization embodiment the charge stock can be a paraffinic stock rich in $C_4$ to $C_8$ normal paraffins, or a normal butane-rich stock, or a n-hexane-rich stock, or a mixture of xylene isomers, etc. In a dehydrogenation embodiment, the charge stock can be any of the known dehydrogenatable hydrocarbons such as an aliphatic compound containing 2 to 30 carbon atoms per molecule, a $C_4$ to $C_{30}$ normal paraffin, a $C_8$ to $C_{12}$ alkylaromatic, a naphthene, and the like. In hydrocracking embodiments, the charge stock will be typically a gas oil, heavy cracked cycle oil, etc. In addition, alkylaromatic and naphthenes can be conveniently isomerized by using the catalyst of the present invention. Likewise, pure hydrocarbons or substantially pure hydrocarbons can be converted to more valuable products by using the trimetallic catalyst of the present invention in any of the hydrocarbon conversion processes, known to the art, that use a dual-function catalyst.

In a reforming embodiment, it is generally preferred to utilize the novel trimetallic catalytic composite in a substantially water-free environment. Essential to the achievement of this condition in the reforming zone is the control of the water level present in the charge stock and the hydrogen stream which is being charged to the zone. Best results are ordinarily obtained when the total amount of water entering the conversion zone from any source is held to a level less than 50 ppm. and preferably less than 20 ppm.; expressed as weight of equivalent water in the charge stock. In general, this can be accomplished by careful control of the water present in the charge stock and in the hydrogen stream. The charge stock can be dried by using any suitable drying means known to the art such as a conventional solid adsorbent having a high selectivity for water; for instance, sodium or calcium crystalline aluminosilicates, silica gel, activated alumina, molecular sieves, anhydrous calcium sulfate, high surface area sodium, and the like adsorbents. Similarly, the water content of the charge stock may be adjusted by suitable stripping operations in a fractionation column or like device. And in some cases, a combination of adsorbent drying and distillation drying may be used advantageously to effect almost complete removal of water from the charge stock. Preferably, the charge stock is dried to a level corresponding to less than 20 ppm. of $H_2O$ equivalent. In general, it is preferred to dry the hydrogen stream entering the hydrocarbon conversion zone down to a level of about 10 vol. ppm. of water or less. This can be conveniently accomplished by contacting the hydrogen stream with a suitable desiccant such as those mentioned above.

In the reforming embodiment, an effluent stream is withdrawn from the reforming zone and passed through a cooling means to a separation zone, typically maintained at about 25° to 150° F., wherein a hydrogen-rich gas is separated from a high octane liquid product, commonly called an unstabilized reformate. When a super-dry operation is desired, at least a portion of this hydrogen-rich gas is withdrawn from the separating zone and passed through an adsorption zone containing an adsorbent selective for water. The resultant substantially water-free hydrogen stream can then be recycled through suitable compressing means back to the reforming zone. The liquid phase from the separating zone is typically withdrawn and commonly treated in a fractionating system in order to adjust the butane concentration, thereby controlling frontend volatility of the resulting reformate.

The conditions utilized in the numerous hydrocarbon conversion embodiments of the present invention are those customarily used in the art for the particular reaction, or combination of reactions, that is to be effected. For instance, alkylaromatic and paraffin isomerization conditions include: a temperature of about 32° to about 1000° F. and preferably about 75° to about 600° F.; a pressure of atmospheric to about 100 atmospheres; a hydrogen to hydrocarbon mole ratio of about 0.5:1 to about 20:1, and a LHSV (calculated on the basis of equivalent liquid volume of the charge stock contacted with the catalyst per hour divided by the volume of conversion zone containing catalyst) of about 0.2 hr.$^{-1}$ to 10 hr.$^{-1}$. Dehydrogenation conditions include: a temperature of about 700° to about 1,250° F., a pressure of about 0.1 to about 10 atmospheres, a liquid hourly space velocity of about 1 to 40 hr.$^{-1}$, and a hydrogen to hydrocarbon mole ratio of about 1:1 to 20:1. Likewise, typically hydrocracking conditions include: a pressure of about 500 psig. to about 3,000 psig.; a temperature of about 400° to about 900° F.; an LHSV of about 0.1 hr.$^{-1}$ to about 10 hr.$^{-1}$; and hydrogen circulation rates of about 1000 to 10,000 SCF per barrel of charge.

In the reforming embodiment of the present invention, the pressure utilized is selected from the range of about 0 psig. to about 1,000 psig., with the preferred pressure being about 50 psig. to about 600 psig. Particularly good results are obtained at low pressure; namely, a pressure of about 50 to 350 psig. In fact, it is a singular advantage of the present invention that it allows stable operation at lower pressure than have heretofore been successfully utilized in so-called "continuous" reforming systems (i.e. reforming for periods of about 15 to about 200 or more barrels of charge per pound of catalyst without regeneration) with all platinum monometallic catalysts. In other words, the trimetallic catalyst of the present invention allows the operation of a continuous reforming system to be conducted at lower pressure (i.e. 100 to about 350 psig.) for about the same or better catalyst life before regeneration as has been heretofore realized with conventional monometallic catalysts at higher pressures (i.e. 400 to 600 psig.). On the other hand, the stability feature of the present invention enables reforming operations conducted at pressures of 400 to 600 psig. to achieve substantially increased catalyst life before regeneration.

Similarly, the temperature required for reforming is generally lower than that required for a similar reforming operation using a high quality catalyst of the prior art. This significant and desirable feature of the present invention is a consequence of the selectivity of the trimetallic catalyst of the present invention for the octane-upgrading reactions that are preferably induced in a typical reforming operation. Hence, the present invention requires a temperature in the range of from about 800° to about 1100° F., and preferably about 900° to about 1050° F. As is well known to those skilled in the continuous reforming art, the initial selection of the temperature within this broad range is made primarily as a function of the desired octane of the product reformate considering the characteristics of the charge stock and of the catalyst. Ordinarily, the temperature then is thereafter slowly increased during the run to compensate for the inevitable deactivation that occurs to provide a constant product. Therefore, it is a feature of the present invention that the rate at which the temperature is increased in order to maintain a constant octane product, is substantially lower for the catalyst of the present invention than for a high quality reforming catalyst which is manufactured in exactly the same manner as the catalyst of the present invention except for the inclusion of the iridium and germanium components. Moreover, for the catalyst of the present invention, the $C_5+$ yield loss for a given temperature increase is substantially lower than for a high quality reforming catalyst of the prior art. In addition, hydrogen production is substantially higher.

The reforming embodiment of the present invention also typically utilizes sufficient hydrogen to provide an amount of about 1 to about 20 moles of hydrogen per mole of hydrocarbon entering the reforming zone, with excellent results being obtained when about 5 to about 10 moles of hydrogen are used per mole of hydrocarbon. Likewise, the liquid hourly space velocity (LHSV) used in reforming is selected from the range of about 0.1 to about 10 hr.$^{-1}$, with a value in the range of about 1 to about 5 hr.$^{-1}$ being preferred. In fact, it is a feature of the present invention that it allows operations to be conducted at higher LHSV than normally can be stably achieved in a continuous reforming process with a high quality reforming catalyst of the prior art. This last feature is of immense economic significance because it allows a continuous reforming process to operate at the same throughput level with less catalyst inventory than that heretofore used with conventional reforming catalysts at no sacrifice in catalyst life before regeneration.

The following working examples are given to illustrate further the preparation of the trimetallic catalytic composite of the present invention and the use thereof in the conversion of hydrocarbons. It is understood that the examples are intended to be illustrative rather than restrictive.

EXAMPLE I

This example demonstrates a particularly good method of preparing the preferred catalytic composite of the present invention.

An alumina carrier material comprising 1/16 inch spheres is prepared by: forming an aluminum hydroxyl chloride sol by dissolving substantially pure aluminum pellets in a hydrochloric acid solution, adding hexamethylenetetramine to the resulting sol, gelling the resulting solution by dropping it into an oil bath to form spherical particles of an aluminum hydrogel, aging and washing the resulting particles to form spherical particles of gamma-alumina containing about 0.3 wt. % combined chloride. Additional details as to this method of preparing the preferred carrier material are given in the teachings of U.S. Pat. No. 2,620,314.

A measured amount of germanium tetrachloride is dissolved in anhydrous ethanol. The resulting solution is then aged at room temperature until an equilibrium condition is established therein. An aqueous solution containing chloroplatinic acid, chloroiridic acid, and hydrogen chloride is then prepared. The two solutions are then intimately admixed and used to impregnate the gamma-alumina particles in amounts, respectively, calculated to result in a final composite containing, on an elemental basis, 0.375 wt. % platinum, 0.375 wt. % iridium, and 0.5 wt. % germanium. In order to insure uniform distribution of the metallic components throughout the carrier material, the amount of hydrogen chloride corresponds to about 2 wt. % of the alumina particles. This impregnation step is performed by adding the carrier material particles to the impregnation mixture with constant agitation. In addition, the volume of the solution is approximately the same as the volume of the carrier material particles. The impregnation mixture is maintained in contact with the carrier material particles for a period of about one-half hour at a temperature of about 70° F. Thereafter, the temperature of the impregnation mixture is raised to about 225° F. and the excess solution is evaporated in a period of about 1 hour. The resulting dried particles are then subjected to a calcination treatment in an air atmospheres at a temperature of about 925° F. for about 1 hour. The calcined spheres are then contacted with an air stream containing $H_2O$ and HCl in a mole ratio of about 40:1 for about 4 hours at 975° F. in order to adjust the halogen content of the catalyst particles to a value of about 0.90.

The resulting catalyst particles are analyzed and found to contain on an elemental basis, about 0.375 wt. % platinum, about 0.375 wt. % iridium, about 0.5 wt. % germanium, and about 0.85 wt. % chloride. For this catalyst, the atomic ratio of germanium to platinum is 3.56:1 and the atomic ratio of iridium to platinum is 1.02:1.

Thereafter, the catalyst particles are subjected to a dry prereduction treatment designed to reduce the platinum and iridium components to the elemental state while maintaining the germanium component in a positive oxidation state by contacting them for 1 hour with a substantially pure hydrogen stream containing less than 5 vol. ppm. $H_2O$ at a temperature of about 1050° F., a pressure slightly above atmospheric and a flow rate of the hydrogen-stream through the catalyst particles corresponding to a gas hourly space velocity of about 720 hr.$^{-1}$.

The resulting reduced catalyst particles are then contacted with a sulfiding gas comprising a mixture of $H_2S$ and $H_2$ in a mole ratio of about 1:10 at a temperature of about 1000° F., atmospheric pressure and GHSV of about 800 hr.$^{-1}$ for a period effective to incorporate about 0.1 wt. % sulfur.

EXAMPLE II

A portion of the spherical trimetallic sulfided catalyst particles produced by the method described in Example I are loaded into a scale model of a continuous, fixed bed reforming plant of conventional design. In this plant a heavy Kuwait naphtha and hydrogen are continuously contacted at reforming conditions: a liquid hourly space velocity of 1.5 hr.$^{-1}$, a pressure of 100 psig., a hydrogen to hydrocarbon mole ratio of 8.1, and a temperature sufficient to continuously produce a $C_5+$ reformate of 102 F-1-clear. It is to be noted that these are exceptionally severe conditions.

The heavy Kuwait naphtha has an API gravity at 60° F. of 60.4, an initial boiling point of 184°, a 50% boiling point of 256°, and an end boiling point of 360° F. In addition, it contains about 8 vol. % aromatics, 71 vol. % paraffins, 21 vol. % naphthenes, 0.5 wt. parts per million sulfur, and 5 to 8 wt. parts per million water. The F-1 clear octane number of the raw stock is 40.0.

The fixed bed reforming plant is made up of a reactor containing the trimetallic catalyst, a hydrogen separation zone, a debutanizer column, and suitable heating, pumping, cooling, and controlling means. In this plant, a hydrogen recycle stream and the charge stock are commingled and heated to the desired temperature. The resultant mixture is then passed downflow into a reactor containing the trimetallic catalyst as a fixed bed. An effluent stream is then withdrawn from the bottom of the reactor, cooled to about 55° F. and passed to a separating zone wherein a hydrogen-rich gaseous phase separates from a liquid hydrocarbon phase. A portion of the gaseous phase is continuously passed through a high surface area sodium scrubber and the resulting water-free hydrogen stream recycled to the reactor in order to supply hydrogen thereto, and the excess hydrogen over that needed for plant pressure is recovered as excess separate gas. The liquid hydrocarbon phase from the hydrogen separating zone is withdrawn therefrom and passed to a debutanizer column of conventional design wherein light ends are taken overhead as debutanizer gas and a $C_5+$ reformate stream recovered as bottoms.

The test run is continued for a catalyst life of about 20 barrels of charge per pound of catalyst utilized, and it is determined that the activity, selectivity, and stability of the present sulfided trimetallic catalyst are vastly superior to those observed in a similar type test with a conventional commercial reforming catalyst. More specifically, the results obtained from the subject catalyst are superior to the platinum metal-contining catalyst of the prior art in the areas of hydrogen production, $C_5+$ yield at octane, average rate of temperature increase necessary to maintain octane, and $C_5+$ yield decline rate. Also it is noted that the principal effect of the sulfiding step on the performance of the instant catalyst involves diminished undesired exothermic hydrocracking and demethylation activity during the initial portion of the test run.

It is intended to cover by the following claims all changes and modifications of the above disclosure of the present invention which would be self-evident to a man of ordinary skill in the catalyst formulation art or the hydrocarbon conversion art.

I claim as my invention:

1. In a process for converting a hydrocarbon which comprises contacting the hydrocarbon at hydrocarbon conversion conditions with a catalytic composite, comprising a porous carrier material containing, on an elemental basis, about 0.01 to about 2 wt. % platinum or palladium, about 0.01 to about 2 wt. % iridium, about 0.01 to about 5 wt. % germanium, and about 0.1 to about 3.5 wt. % halogen, wherein the platinum or palladium, iridium, and germanium are uniformly dispersed throughout the porous carrier material, wherein substantially all of the platinum or palladium and iridium are present in the corresponding elemental metallic states and wherein substantially all of the germanium is present in an oxidation state above that of the elemental metal, the improvement which comprises sulfiding the catalytic composite, prior to contact with the hydrocarbon, by treating the composite with a sulfiding gas at conditions selected in incorporate about 0.05 to about 0.5 wt. % sulfur.

2. An improved process as defined in claim 1 wherein the composite contains about 0.05 to about 1 wt. % platinum, about 0.05 to about 1 wt. % iridium, about 0.05 to about 2 wt. % germanium, and about 0.5 to about 1.5 wt. % halogen.

3. An improved process as defined in claim 1 wherein the contacting of the hydrocarbon with the catalytic composite is preformed in the presence of hydrogen.

4. An improved process as defined in claim 1 wherein the type of hydrocarbon conversion is catalytic reforming of a gasoline fraction to produce a high octane reformate, wherein the hydrocarbon is contained in the gasoline fraction, wherein the contacting is performed in the presence of hydrogen, and wherein the hydrocarbon conversion conditions are reforming conditions.

5. An improved process as defined in claim 4 wherein the reforming conditions include a temperature of about 800° to about 1100° F., a pressure of about 0 to about 1,000 psig., a liquid hourly space velocity of about 0.1 to about 10 hr.$^{-1}$, and a mole ratio of hydrogen to hydrocarbon of about 1:1 to about 20:1.

6. An improved process as defined in claim 1 wherein the sulfiding gas is a mixture of hydrogen and hydrogen sulfide.

7. An improved process as defined in claim 1 wherein the sulfiding conditions include a temperature of about 50° to about 1150° F.

8. A sulfided catalytic composite comprising a porous carrier material containing, on an elemental basis, about 0.01 to about 2 wt. % platinum or palladium metal, about 0.01 to about 2 wt. % iridium metal, about 0.01 to about 5 wt. % germanium, about 0.1 to about 3.5 wt. % halogen and about 0.05 to about 0.5 wt. % sulfur, wherein the platinum or palladium, germanium, and iridium are uniformly dispersed throughout the porous carrier material, wherein substantially all of the platinum or palladium and iridium were present in the corresponding elemental metallic state prior to the composite being sulfided, wherein substantially all of the germanium was present in an oxidation state above that of the elemental metal prior to the composite being sulfided.

* * * * *